United States Patent [19]

Farling et al.

[11] Patent Number: 4,660,755

[45] Date of Patent: Apr. 28, 1987

[54] METHOD FOR CONSTRUCTING A SURGICAL IMPLANT

[75] Inventors: Gene M. Farling, Warsaw; Jack E. Parr, North Webster; Arden R. Zolman, Warsaw, all of Ind.

[73] Assignee: Zimmer, Inc., Warsaw, Ind.

[21] Appl. No.: 773,909

[22] Filed: Sep. 9, 1985

[51] Int. Cl.⁴ .............................................. A61F 1/24
[52] U.S. Cl. ..................................... 228/178; 623/18; 219/86.1
[58] Field of Search ...................... 623/16, 18, 20, 22, 623/23; 228/193, 178; 219/86.1

[56] References Cited

U.S. PATENT DOCUMENTS

| | | | |
|---|---|---|---|
| 2,866,886 | 12/1958 | Koehring | 219/117 |
| 3,789,498 | 2/1974 | Cole | 228/193 |
| 3,905,777 | 9/1975 | Lacroix | 29/183.5 |
| 4,038,703 | 8/1977 | Bokros | 623/18 |
| 4,064,567 | 12/1977 | Burstein et al. | 623/18 |
| 4,261,063 | 4/1981 | Blanquaert | 3/1.91 |
| 4,406,023 | 9/1983 | Harris | 623/16 |
| 4,495,664 | 1/1985 | Blanquaert | 3/1.913 |
| 4,570,271 | 2/1986 | Sump | 623/18 |

FOREIGN PATENT DOCUMENTS 2142544 1/1985 United Kingdom .

Primary Examiner—M. Jordan
Attorney, Agent, or Firm—Paul David Schoenle

[57] ABSTRACT

A method for constructing a surgical implant provides a porous layer that is metallurgically bonded to a substrate. An electrode passes current through the porous layer and through the substrate while also controlling the compaction of the porous layer relative to the substrate.

1 Claim, 5 Drawing Figures

METHOD FOR CONSTRUCTING A SURGICAL IMPLANT

The present invention relates to a method for constructing a surgical implant, such as a hip prosthesis, wherein a substrate material is adapted to transmit loads imparted to a skeletal structure and a porous surface is provided on the substrate to enhance biological fixation to the skelatal structure.

A porous coated hip prosthesis is illustrated in U.S. Pat. No. 4,495,664. In this patent a porous coating or layer of titanium wire is fixedly secured to a substrate pin via a strip which is spot welded in numerous locations to trap the titanium wire between the pin and the strip. In the absence of a spot weld, it has been proposed to subject the substrate and porous coating to thermal energy in a furnace so that a bond is established when the substrate and porous coating melt together at points of contact. In U.S. Pat. No. 3,905,777, a porous coating in the form of a wire screen is secured to a substrate pin by a plurality of welds fixedly securing the wire screen to itself and to the substrate pin.

When a thermal bond is established in a furnace at high temperatures, the microstructure of the substrate is changed so that the load capabilities thereof are diminished. Consequently, it is desirable to maintain the furnace at a low temperature and cycle the thermal bond for a longer period of time in the low temperature furnace. As a result the manufacturing time for the surgical implant heretofore disclosed is longer than desired.

When the porous layer is welded to the substrate it has been proposed to use electron beam welding. However, this approach requires numerous applications to securely fasten the porous layer to the substrate and further requires the porous layer to be fastened together in a predetermined geometry before the porous layer is juxtapositoned the substrate.

In view of the aforegoing problems with the fixation of a porous layer to a substrate for a surgical implant, the present invention teaches a method of establishing a metallurgical bond between individual elements of the porous layer and between the porous layer and the substrate via resistance welding. An electrode is designed to substantially match the contour of the porous layer so that when the electrode is engageable with the porous layer it is possible to conduct current throughout the porous layer to the substrate in a short period of time. As the current is conducted through the porous layer, the individual elements thereof are heated at the points of contact to metallurgically bond the elements together.

Similarly, the individual elements of the porous surface which are engaged with the substrate are also heated at the point of contact with the substrate to metallurgically bond these elements to the substrate. It is noted that the heat build up generated by the resistance welding is concentrated at the points of contact rather than throughout the individual elements or throughout the substrate.

It is an object of the present invention to provide a method for constructing a surgical implant that is less time consuming and at the same time substantially avoids any deleterious changes in the microstructure of the substrate.

One form of the invention is illustrated in the accompanying drawings wherein

Figures 1, 2, 3, 4, 5:
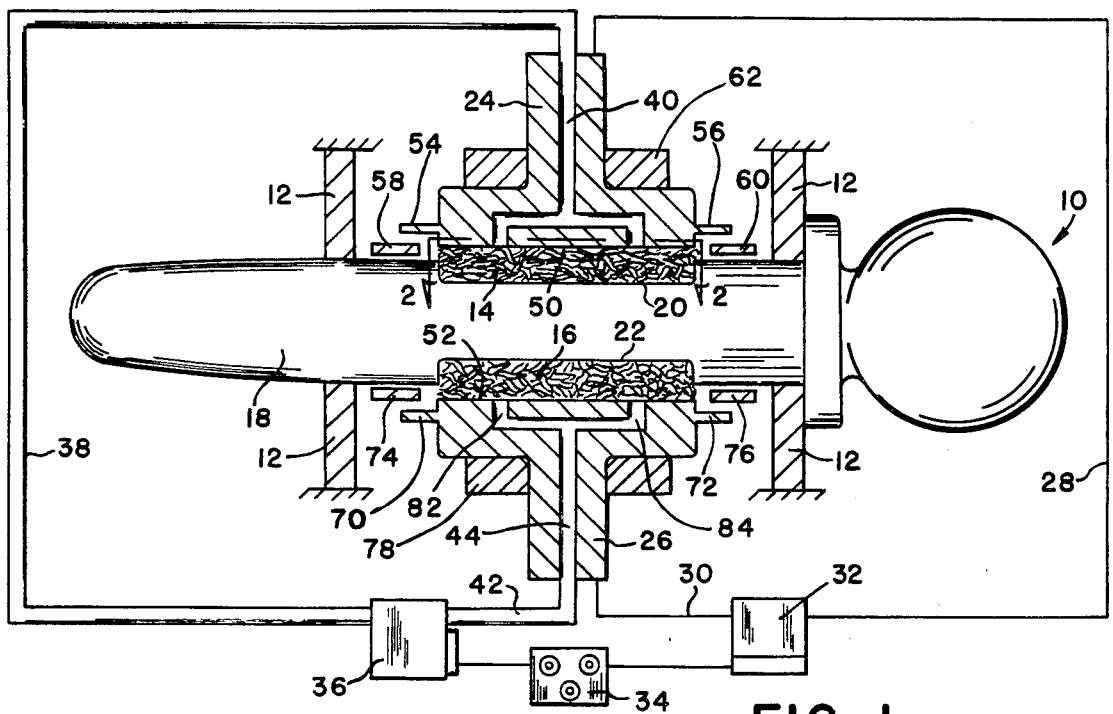
FIG. 1 is a schematic illustration of the process contemplated by the present invention.
FIG. 2 is a cross sectional view taken along line 2—2 of FIG. 1.
FIG. 3 is a top view of the surgical implant illustrated in FIG. 1.
FIG. 4 is a partial view of FIG. 1 prior to metallurgical bonding.
FIG. 5 is a view similar to FIG. 4 but illustrating the parts after metallurgical bonding.

A surgical implant 10, such as a hip prosthesis, is retained in a plurality of fixtures 12 so that a porous layer 14, and a porous layer 16 can be affixed to a substrate 18 of the surgical implant 10. The substrate 18 is provided with a recess 20 for receiving porous layer 14 and a recess 22 for receiving porous layer 16. An electrode 24 opposes the porous layer 14 and an electrode 26 opposes the porous layer 16. Each electrode 24 and 26 is connected via respective wires 28 and 30, with a power source or current generator 32. A control panel 34 selectively operates the current generator and also controls the operation of a gas reservoir 36. The gas reservoir 36 communicates via conduit 38 with an opening 40 in electrode 24 and via conduit 42 with an opening 44 in electrode 26.

The electrode 24 forms an outer surface 50 opposing the porous layer 14 and defining a contour substantially matching a contour defined by the porous layer 14. Similarly, the electrode 26 forms an outer surface 52 opposing the porous layer 16 and defining a contour substantially matching a contour defined by the porous layer 16. The electrode 24 includes a pair of flanges 54 and 56 which face a pair of stops 58 and 60, respectively. An advancement device 62 surrounds the electrode 24 to oppose a shoulder 64 for the purpose of moving the electrode 24 toward the porous layer 14 until the pair of flanges 54 and 56 are engageable with the pair of stops 58 and 60, respectively. The opening 40 is bifurcated to form two apertures 66 and 68 leading to the outer surface 50. Additional apertures may be provided if desired. The electrode 26 also includes a pair of flanges 70 and 72 which face a pair of stops 74 and 76. An advancement device 78 cooperates with the electrode 26 via shoulder 80 to move the electrode 26 toward the porous layer 16 until the pair of flanges 70 and 72 are engageable with the pair of stops 74 and 76, respectively. The opening 44 is bifurcated to define a pair of apertures 82 and 84 leading to the outer surface 52. Additional apertures may be provided in the electrode 26.

In order to construct the surgical implant 10, the substrate 18 is disposed within the fixtures 12 and the porous layers 14 and 16 are positioned within the cavities 20 and 22, respectively. Alternatively, the porous layers 14 and 16 could be disposed in the cavities 20 and 22 prior to disposition of the substrate 18 within the fixture 12. Next, the control panel 34 is sequenced to cycle the current generator 32, the gas reservoir 36, and the advancement devices 62 and 78.

The advancement devices 62 and 78 move the electrodes 24 and 26 toward the substrate 18 to tightly compact the porous layers 14 and 16 in their respective cavities 20 and 22.

Current from the current generator 32 is conducted via wires 28 and 30 to electrodes 24 and 26, through the porous layers 14 and 16, and through the substrate 18. As the current flows through the porous layers, heat is generated at the points of contact so that surface metallurgical bonding occurs between the porous layers and also between the porous layers and the substrate. At the same time, the electrodes are further advanced toward the substrate to compact the porous surfaces 14 and 16. Viewing FIGS. 4 and 5, the electrode 24 defines a spacing A with the stop 60 when the electrode is initially engageable with the porous layer 14 and this spacing is completely taken up at the end of the current generator cycle. Consequently, the degree of compactness for the porous layer 14 is controlled by the position of the flanges 54 and 56 and the stops 58 and 60. Furthermore, the current is conducted through the porous layer 14 as the electrode 24 is being moved by the advancement mechanism 62. Also, when the control panel 34 is operated, the gas reservoir 36 communicates an inert gas via the apertures 66, 68, 82 and 84 to the porous layers 14 and 16 to substantially prevent, or diminish, oxygen discoloration during metallurgical bonding. The time required to fixedly secure the porous layers to the substrate varies from thirty (30) seconds to one hundred eighty (180) seconds depending on the size of the porous layer.

In a preferred embodiment, the porous layers 14 and 16 comprise a titanium fiber metal pad such as disclosed in U.S. Pat. No. 3,906,550 issued to Rostoker and Galante and the substrate 18 is made from titanium.

We claim:

1. A method for constructing a surgical implant wherein a biologically compatible substrate is adapted for transmitting loads imparted to a skeletal structure of an animal or human and a porous layer is coupled to the substrate to enhance biological fixation of the implant relative to the skeletal structure, the method comprising the steps of disposing the porous layer adjacent to the substrate and subjecting the porous layer and the substrate to metallurgical bonding by transmitting a current through the porous layer and the substrate so that all of the porous layer is metallurgically bonded together at points of contact therebetween to form a porous surface and the porous layer is metallurgically bonded to the substrate at the points of contact therebetween, the metallurgical bonding takes place in the absence of a furnace to substantially avoid heat build up throughout the substrate and substantially confine heat build up at the points of contact, and the metallurgical bonding occurs via an electrode engageable with the porous layer and the electrode is moved toward the porous layer while current is transmitted to the porous layer and the substrate, and movement of the electrode is limited independently of the porous layer to a predetermined distance.

* * * * *